United States Patent
Kotz et al.

(10) Patent No.: US 9,595,187 B2
(45) Date of Patent: Mar. 14, 2017

(54) WEARABLE COMPUTING DEVICE FOR SECURE CONTROL OF PHYSIOLOGICAL SENSORS AND MEDICAL DEVICES, WITH SECURE STORAGE OF MEDICAL RECORDS, AND BIOIMPEDANCE BIOMETRIC

(71) Applicant: THE TRUSTEES OF DARTMOUTH COLLEGE, Hanover, NH (US)

(72) Inventors: David Kotz, Lyme, NH (US); Ryan Halter, Orford, NH (US); Cory Cornelius, Portland, OR (US); Jacob Sorber, Clemson, SC (US); Minho Shin, Yongin-si (KR); Ronald Peterson, Brattleboro, VT (US); Shrirang Mare, West Lebanon, VT (US); Aarathi Prasad, Lebanon, NH (US); Joseph Skinner, Manchester, NH (US); Andres David Molina-Markham, White River Jct., VT (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 183 days.

(21) Appl. No.: 14/312,316

(22) Filed: Jun. 23, 2014

(65) Prior Publication Data
US 2014/0300490 A1 Oct. 9, 2014

Related U.S. Application Data

(63) Continuation-in-part of application No. PCT/US2012/071566, filed on Dec. 24, 2012.
(Continued)

(51) Int. Cl.
*A61B 5/00* (2006.01)
*G08C 17/02* (2006.01)
(Continued)

(52) U.S. Cl.
CPC .......... *G08C 17/02* (2013.01); *A61B 5/0028* (2013.01); *A61B 5/053* (2013.01); *G06F 19/323* (2013.01);
(Continued)

(58) Field of Classification Search
CPC ........ A61B 5/0024; A61B 5/00; A61B 5/0015
(Continued)

(56) References Cited

U.S. PATENT DOCUMENTS 6,643,531 B1 * 11/2003 Katarow .............. A61B 5/1172
600/323
2006/0189924 A1 8/2006 Blakley et al.
(Continued)

FOREIGN PATENT DOCUMENTS

KR 1020070085856 A 8/2007
KR 1020110042811 A 4/2011

OTHER PUBLICATIONS

PCT Application PCT/US2012/071566 International Search Report and Written Opinion dated Apr. 29, 2013, 15 pages.
(Continued)

*Primary Examiner* — Kevin Kim
(74) *Attorney, Agent, or Firm* — Lathrop & Gage LLP

(57) ABSTRACT

A wearable master electronic device (Amulet) has a processor with memory, the processor coupled to a body-area network (BAN) radio and uplink radio. The device has firmware for BAN communications with wearable nodes to receive data, and in an embodiment, send configuration data. The device has firmware for using the uplink radio to download apps and configurations, and upload data to a
(Continued)

server. An embodiment has accelerometers in Amulet and wearable node, and firmware for using accelerometer readings to determine if node and Amulet are worn by the same subject. Other embodiments use pulse sensors or microphones in the Amulet and node to both identify a subject and verify the Amulet and node are worn by the same subject. Another embodiment uses a bioimpedance sensor to identify the subject. The wearable node may be an insulin pump, chemotherapy pump, TENS unit, cardiac monitor, or other device.

26 Claims, 4 Drawing Sheets

Related U.S. Application Data

(60) Provisional application No. 61/580,102, filed on Dec. 23, 2011, provisional application No. 61/655,893, filed on Jun. 5, 2012.

(51) Int. Cl.
  *A61B 5/053* (2006.01)
  *G06F 19/00* (2011.01)
(52) U.S. Cl.
  CPC ........ *G06F 19/3418* (2013.01); *A61B 5/7267* (2013.01); *G06F 19/3406* (2013.01); *G06F 19/3412* (2013.01)

(58) Field of Classification Search
  USPC ................................ 340/521, 539.12, 573.1
  See application file for complete search history.

(56) References Cited

U.S. PATENT DOCUMENTS

| | | |
|---|---|---|
| 2008/0294020 A1 | 11/2008 | Sapounas |
| 2009/0023391 A1 | 1/2009 | Falck |
| 2009/0069642 A1* | 3/2009 | Gao .................. A61B 5/02055 600/300 |
| 2010/0204596 A1* | 8/2010 | Knutsson ........... A61B 5/02055 600/509 |
| 2011/0152629 A1* | 6/2011 | Eaton .................. G06F 19/3406 600/300 |
| 2012/0146796 A1* | 6/2012 | Margon .................... A61B 5/05 340/573.1 |
| 2013/0144536 A1* | 6/2013 | Baker .................. A61B 5/7203 702/19 |

OTHER PUBLICATIONS

PCT Application PCT/US2012/071566 Response to Written Opinion filed Oct. 23, 2013, 14 pages.
Ullah, Sana, et al., "A Comprehensive Survey of Wireless Body Area Networks," J Med Sheet, DOI 10.107/s10916-010-9571-3, Aug. 19, 2010, 30 pages.
O'Brien, "Tiny RFID Amulet Stores Medical Records, Makes Paramedics' Lives Easier," Engadget, Retrieved at http://www.engadget.com/2011/08/08/tiny-rfid-amulet-stores-medical-records-makes-paramedics-lives/, Aug. 8, 2011, 6 pages.

* cited by examiner

WEARABLE COMPUTING DEVICE FOR SECURE CONTROL OF PHYSIOLOGICAL SENSORS AND MEDICAL DEVICES, WITH SECURE STORAGE OF MEDICAL RECORDS, AND BIOIMPEDANCE BIOMETRIC

RELATED APPLICATIONS

The present application is a continuation-in-part of International Application No. PCT/US2012/071566 filed 24 Dec. 2012 which claims the benefit of priority to co-owned U.S. Provisional Patent Application 61/580,102 filed 23 Dec. 2011 and U.S. Provisional Patent Application 61/655,893 filed 5 Jun. 2012. All of these applications are hereby incorporated by reference in their entireties and have at least one inventor in common.

GOVERNMENT RIGHTS

This invention was made with US Federal government support under grant numbers 0910842 and 1143548 awarded by the National Science Foundation (NSF), and grant number 90TR0003-01 awarded by the Department of Health and Human Services (HHS-ONC). The United States government has certain rights in the invention.

BACKGROUND

Several suppliers are producing devices for monitoring the health and activity of individuals. For example, the Fitbit Ultra® (trademark of Fitbit, Inc. 625 Market Street, Suite 1400, San Francisco, Calif.) is a wearable electronic device that monitors a person's or patient's activity levels through a combination of accelerometers and altimeters, and reports that activity wirelessly through a base station attached to an internet-connected computer to a server. Lumoback® (Trademark of zero2one, Palo Alto, Calif.) monitors posture, transmitting postural information wirelessly to a cell phone, allowing an application (app) running on the cell phone to nag a subject into "sitting up straight".

Wearable cardiac monitor devices that record heart-rate data from a person throughout a day for later retrieval by a physician are known, and commonly used to diagnose arrhythmias.

There have also been proposals for implementing a Body-area network (BAN), or a wireless body-area network (WBAN). S. Ullah, et al. *A Comprehensive Survey of Wireless Body Area Networks: On PHY, MAC, and Network Layers Solutions*, Journal of Medical Systems, 2010, provides a review of existing body-area networks. These networks enable communication between several miniaturized body sensor units (BSU) and a single body central unit (BCU) worn on the human body. In wireless body-area networks (WBAN), a BCU uses short-range, low-power, digital communications protocols such as, but not limited to, Bluetooth® (Trademark of Bluetooth Special Interest Group, Kirkland, Wash.) or Zigbee® (trademark of Zigbee Alliance, San Ramon, Calif.) to communicate with one or more BSUs. The BCU typically collects data from BSUs, then relays that information through a wireless network to a host computer where the information is stored in a database. Most such networks operate in a star configuration, with the BCU communicating directly with each BSU.

We have previously discussed a method for determining when two sensors are attached to the same, or to a different, body by correlating accelerometer readings between the sensors. This method is discussed in Cory Cornelius and David Kotz, *Recognizing whether sensors are on the same body*, in the Proceedings of the Ninth International Conference on Pervasive Computing, San Francisco, Calif. (Jun. 12-15, 2011), and also published as Cory Cornelius and David Kotz. *Recognizing whether sensors are on the same body*. Journal of Pervasive and Mobile Computing, 8(6): 822-836, December, 2012. DOI 10.1016/j.pmcj.2012.06.005 (Cornelius & Kotz) the contents of which are incorporated herein by reference.

With increased memory capacity and portability of programmable electronic devices, a number of suppliers have begun marketing electronic memory-storage devices intended to be worn by a patient and to store key components of a medical record. USB-readable medical-records storage devices are known. USB-FLASH disk-emulators with labels advising physicians to look at their contents and usable for holding emergency medical information are available on the market; some have encryption and require passwords for entry.

Bioimpedance is a physiological property related to a tissue's resistance to electrical current flow and its ability to store electrical charge. In in vivo human applications, it is typically measured through metallic electrodes (transducers) placed on the skin and around an anatomic location of interest, for example, but not limitation the wrist. These electrical properties are predominantly a function of the underlying tissue being gauged, including the specific tissue types present, including blood, adipose, muscle, bone, and other tissue, the anatomic configuration including bone or muscle orientation and quantity, and the state of the tissue, including whether the tissue is edematous or normally hydrated. Significant impedance differences exist between the varying tissue types, anatomic configurations, and tissue state, each of which may provide a unique mechanism for distinguishing between people.

SUMMARY

A wearable device for secure control of physiological sensors and medical devices, with secure storage of medical records, hereinafter the "Amulet," is described herein.

A wearable master electronic device, or Amulet, includes at least one processor with a memory, the processor coupled to a radio subsystem, the radio subsystem further including at least one radio, the radio subsystem configured to provide a body area network (BAN) radio function to communicate with nodes of a BAN and to provide an uplink radio function for communications with a server; the memory further comprising machine-readable instructions capable of directing the processor to communicate through the BAN radio with at least one wearable node to receive data therefrom, and machine-readable instructions capable of directing the processor to communicate through the uplink radio to download specific machine-executable instructions associated with the wearable node and to upload data to a server.

An alternative embodiment of the Amulet or wearable master electronic device includes at least one processor with a memory, the at least one processor being coupled to a radio subsystem; at least one sensor configured for observing a biometric of a wearer, the biometric selected from the group consisting of vocal resonance, and bioimpedance; the memory further including machine-readable instructions capable of directing the processor to execute a classifier, the classifier configured to identify a wearer from wearer records in a database of potential wearers by using biometric sensor readings of a sensor selected from the group consisting of the at least one sensor and a sensor of a wearable node in communication with the wearable node over the radio subsystem.

In another embodiment, the Amulet has a processor with memory, the processor coupled to a body-area network (BAN) radio and uplink radio. The device has firmware for BAN communications with wearable nodes to receive data, and in an embodiment, to send configuration data to wearable nodes. The device has firmware for using the uplink radio to download apps and configurations, and upload data to a server. An embodiment has accelerometers in Amulet and wearable node, and firmware for using accelerometer readings to determine if node and Amulet are worn by the same subject. Other embodiments use pulse sensors or microphones in the Amulet and node to both identify a subject and verify the amulet and node are worn by the same subject. Another embodiment uses a bioimpedance sensor to identify the subject. The wearable node in communication with the Amulet may be an insulin pump, chemotherapy pump, TENS unit, cardiac monitor, or other device.

Another embodiment of the Amulet has a battery-powered processor with a memory, the processor being coupled to a body-area network (BAN) radio and to an uplink radio. The memory has firmware for communicating through the BAN radio with at least one wearable node to receive data, and firmware for communicating through the uplink radio to download apps and configuration information associated with the wearable node and to upload data to a server. In alternative embodiments, the memory has firmware for communicating through the BAN radio to configure one or more of the nodes.

A particular embodiment of the Amulet has a battery-powered processor with a memory, the processor being coupled to a body-area network (BAN) radio and to an uplink radio. This Amulet also has an accelerometer, and firmware for processing readings from both its accelerometer and a second accelerometer in the wearable node to determine if the wearable node and the wearable master electronic device are worn by the same subject.

Particular embodiments add a gyroscope to be used, in embodiments having an accelerometer, to assist in determining if the Amulet and wearable node are worn by the same person, and may also be used in measuring the subject's level of activity, or for recognizing gestures as a means of user control over the Amulet or other wearable nodes in the body-area network.

Particular embodiments add a fingerprint sensor to be used for authenticating the subject or wearer who wears the Amulet.

Particular embodiments use a pulse sensor or microphone to determine if the Amulet and wearable node are worn by the same subject.

Particular embodiments add a small display so the Amulet can convey information to the subject.

Particular embodiments add a speaker, beeper, or internal vibration device so the Amulet can alert the subject.

Particular embodiments have machine readable instructions for using data recorded by one or more of a bioimpedance sensor or a microphone of the Amulet or wearable node to identify in a database of potential wearers an individual wearing the Amulet or wearable node by classifying the data to identify an individual in the database.

The wearable node, or slave node, may be an insulin pump, chemotherapy pump, TENS unit, cardiac monitor, or other device for monitoring physiological or behavioral characteristics of the subject.

DETAILED DESCRIPTION OF THE EMBODIMENTS

A new technique for using microphones with processing for determining vocal resonance and wearer identification is described in the article Cory Cornelius, Zachary Marois, Jacob Sorber, Ron Peterson, Shrirang Mare, and David Kotz, Vocal Resonance as a Biometric for Pervasive Wearable Devices, Technical Report TR2014-747, Dartmouth Computer Science, February, 2014, a draft of which was submitted as an attachment to a parent provisional application to this document (Cornelius, et al.), and a poster presentation by Cory Cornelius and Zachary Marois and Jacob Sorber and Ron Peterson and Shrirang Mare and David Kotz, entitled Passive Biometrics for Pervasive Wearable Devices (Poster paper) In the *Workshop on Mobile Computing Systems and Applications (HotMobile)*, February, 2012. ACM Press, which is also incorporated herein by reference, published after the priority date of the present application, and incorporated herein by reference. Other concepts have been published in Cory Cornelius and David Kotz, Recognizing whether sensors are on the same body, *Journal of Pervasive and Mobile Computing*, 8(6):822-836, December, 2012. DOI 10.1016/j.pmcj.2012.06.005, published after the priority date of the present application, and incorporated herein by reference. A technique for using bioimpedance for wearer identification is described in the an article by coinventors Cory Cornelius, Jacob Sorber, Ronald Peterson, Joe Skinner, Ryan Halter, David Kotz, Who wears me? Bioimpedance as a passive biometric (Cornelius, Sorber, et al), presented at the USENIX Workshop on Health Security and published online at https://www.usenix.org/conference/healthsec12/who-wears-me-bioimpedance-passive-biometric, on Aug. 6, 2012 the contents of which are incorporated herein by reference. Other publications now include Cory T. Cornelius. *Usable Security for Wireless Body-Area Networks*. Ph.D. Thesis, Dartmouth College Computer Science, September, 2013. Available as Dartmouth Computer Science Technical Report TR2011-741, and Cory Cornelius and Ronald Peterson and Joseph Skinner and Ryan Halter and David Kotz. *A wearable system that knows who wears it*. In Proceedings of the International Conference on Mobile Systems, Applications, and Services (MobiSys), June, 2014. Accepted for publication. DOI 10.1145/2594368.2594369, the contents of both are incorporated herein by reference.

Figure 1:
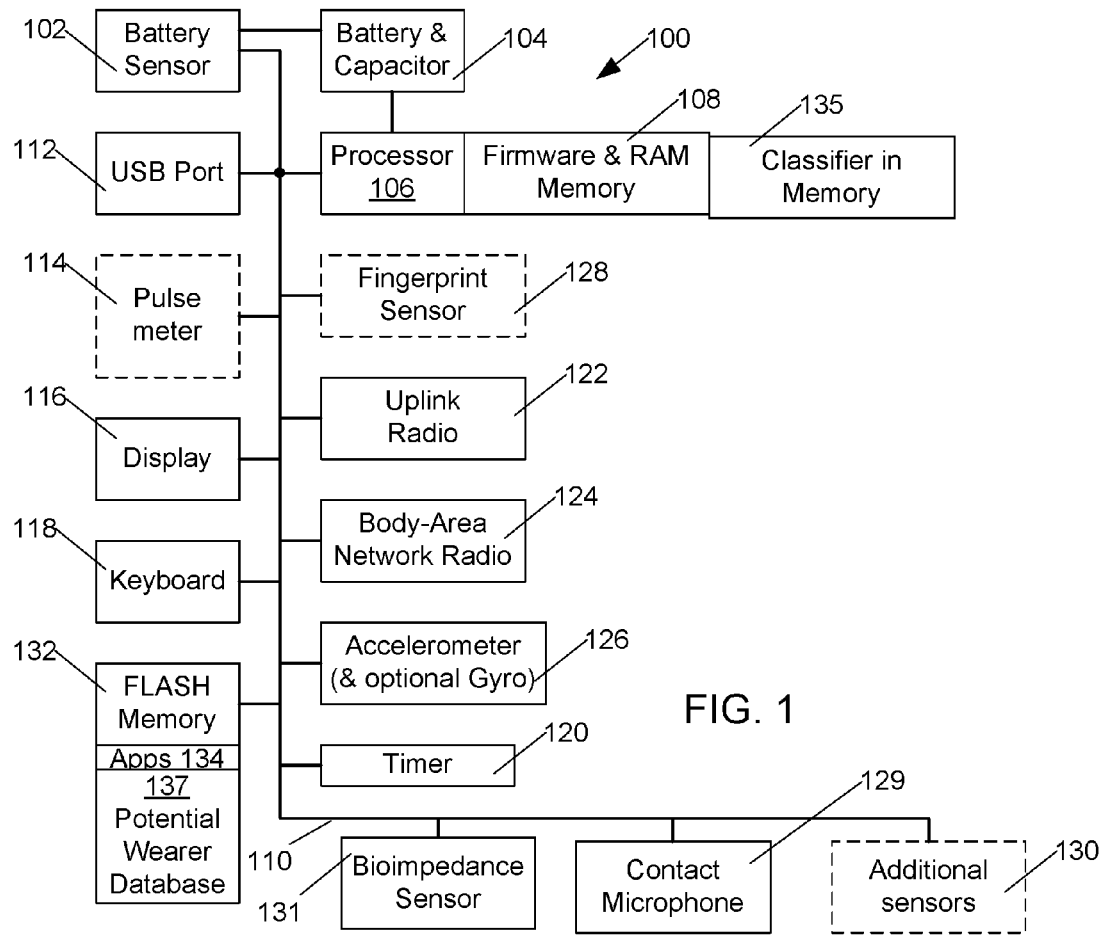
FIG. 1 is a block diagram of an exemplary embodiment of the Amulet, a wearable computing device for secure control of physiological sensors and medical devices, with secure storage of medical records.
Figure 3:
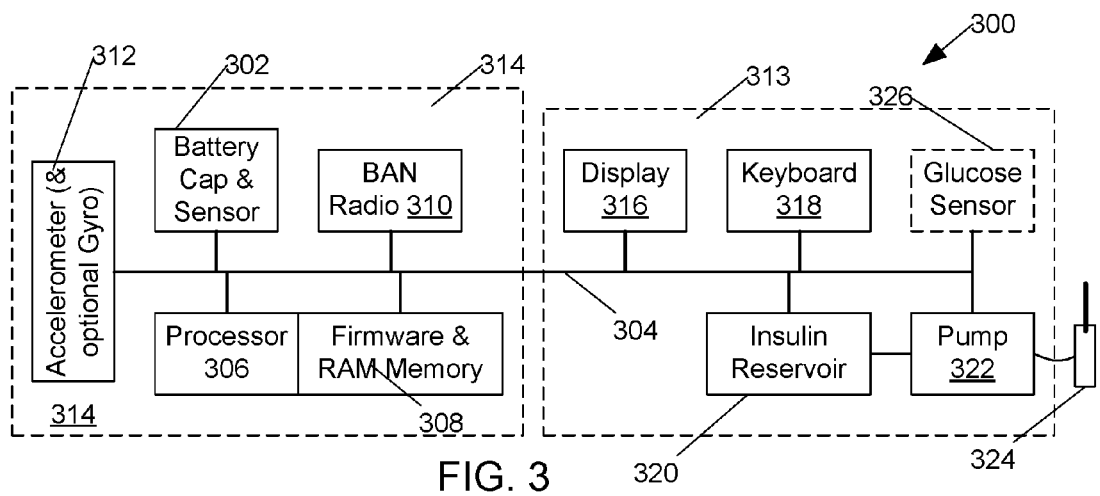
FIG. 3 is a block diagram of an exemplary node for use with the Amulet.

The Amulet 100 (FIG. 1) is a wearable device incorporating a battery voltage sensor 102, a battery 104 for powering the Amulet, a small, low-power, processor 106, and firmware and RAM memory system 108; in an embodiment a capacitor is provided to allow retention of data in RAM memory 108 while battery 104 is changed. Processor 106 communicates over a bus 110 with battery sensor 102, as well as a USB-port interface 112, an optional pulse meter device 114, a small liquid-crystal display 116, a tiny keyboard with a few specific-function keys 118, and a clock-timer circuit 120. In alternative embodiments, displays of other types such as e-ink or even light emitting diode status lamps may be used. Processor 106 also communicates with a Bluetooth or other low-powered uplink digital radio 122 transceiver for communicating with a cellular cell phone (not shown) for relay to a server, or another radio suitable for communications over a network to a server, and one or more Zigbee, 608 MHz Wireless Medical Telemetry Services (WMTS), 402 MHz Medical Implant Communications Service (MICS), the new MBAN band of 40 MHz of spectrum at 2360-2400 MHz regulated in the United States as part of the Medical Device Radiocommunication (MedRadio) Service in Part 95 of FCC rules, or other low-powered digital Body-Area Network (BAN) radios 124 for digital communications with sensor and actuator nodes of a BAN. For purpose of this device, nodes of a BAN under control of the Amulet, which could be referenced as slave nodes because they respond to commands from, but do not control the Amulet, are referred to as wearable nodes. In an embodiment, the Amulet is also equipped with a three-dimensional accelerometer and gyroscope module 126, and in a particular embodiment is also equipped with a fingerprint sensor 128. In an embodiment, the Amulet is also equipped with one or more devices for alerting the wearer, such as a speaker, beeper, or vibration mechanism. Additional sensors 130 may also be included within the Amulet, such as skin temperature and conductivity sensors. In a particular embodiment, a bioimpedance sensing device 131 is included in the Amulet.

In an alternative embodiment, a single radio serves the functions of both the BAN radio 124 for communications with other nodes of the BAN, and the uplink radio 122 for communication directly, or through other devices such as a cell phone that may relay communications from the Amulet through a data network associated with a digital cellular telephone system and thus to and from a server. For purposes of this document, the term radio subsystem includes either separate BAN 124 and uplink 122 radios, or a single radio capable of performing both BAN communications and uplink communications.

Figure 2:
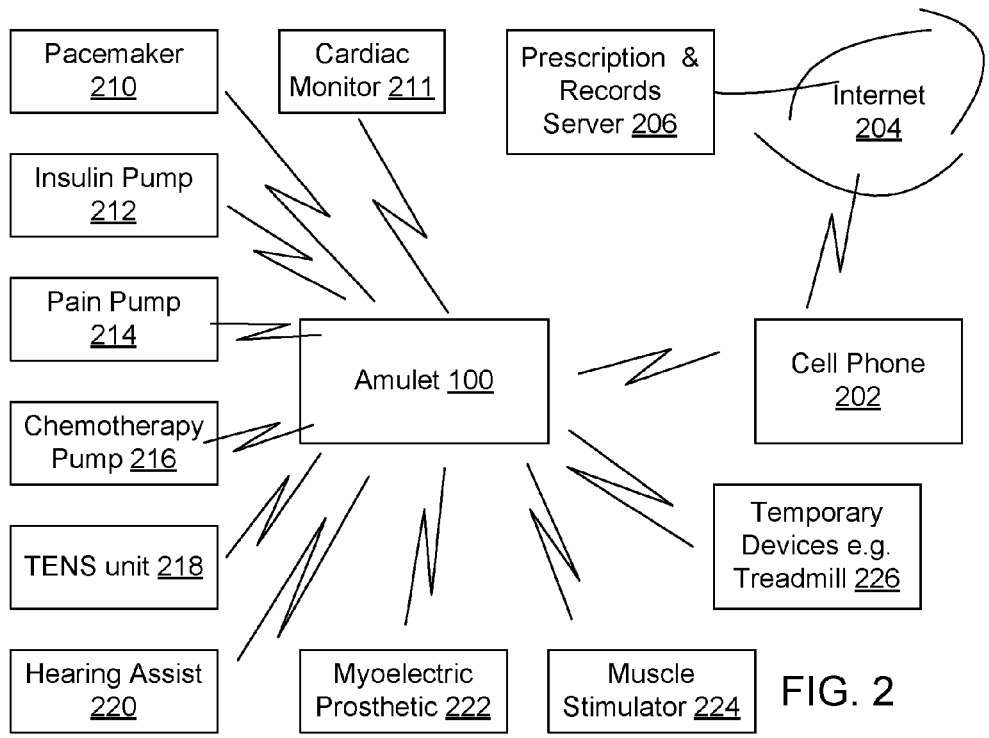
FIG. 2 is a block diagram of an exemplary system incorporating the Amulet with multiple sensors and actuators.
Figure 4:
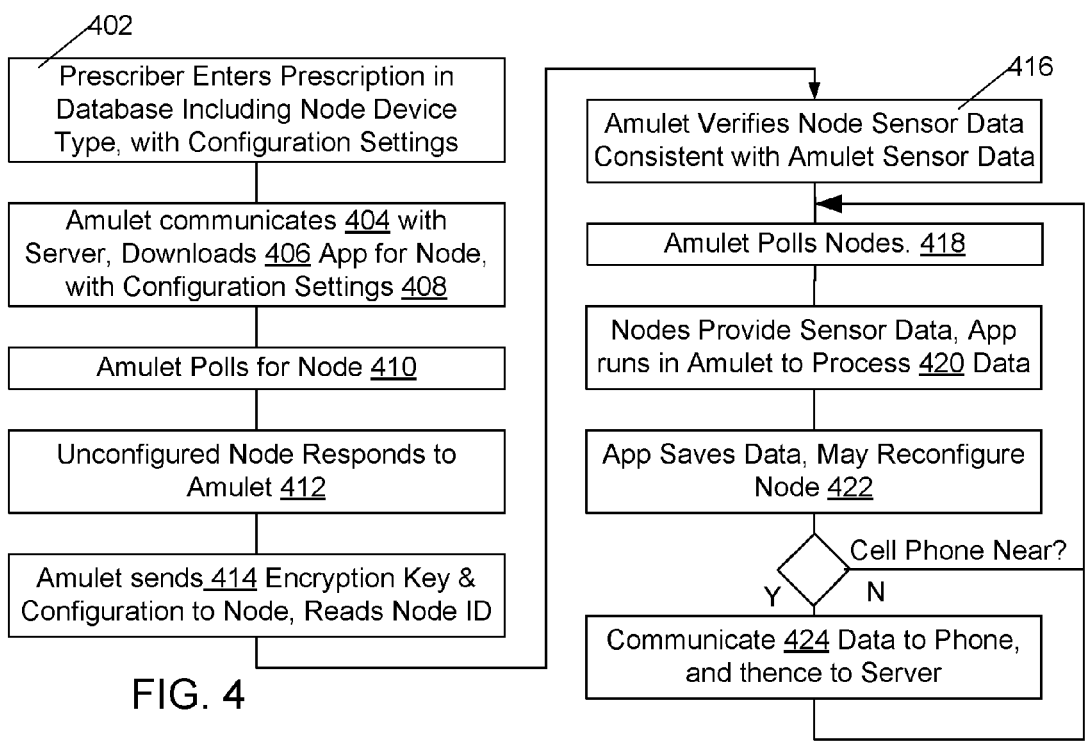
FIG. 4 is a flowchart of adding a node to a body-area network incorporating the Amulet.

In an alternative embodiment for hospital use, or for nonhospital use where a patient desires the Amulet to be capable of uplink transmissions when near an 802.11 network router but not within Bluetooth range of the associated cell phone, the Amulet has a digital communications radio for directly interfacing with wireless local-area computer networks, such as a radio compliant with one or more of the IEEE 802.11 family of Wi-Fi standards, or similar standards, instead of the Bluetooth or other low-powered digital radio 122. It is anticipated that an alternative embodiment may have both a Bluetooth and an 802.11 digital radio for uplink communications, making use of whichever radio offers connectivity when it desires to communicate with a server, such as Prescription & Records server 206 (FIG. 2).

It is known that on some single-processor systems in the general computing art, an ill-behaved app (whether accidentally ill-behaved or purposely ill-behaved like some viruses) running on the processor can interfere with other apps running on the processor. In some embodiments the Amulet 100 has multiple processors 106, or a multiple-core processor chip, to support strong isolation between multiple health-monitoring tasks, preventing a task running on one processor from interfering with tasks on other processors. In a particular embodiment, firmware for basic operation of the Amulet, its communications and security protocols, is assigned to run on one processor, while an app associated with a critical node is assigned to run on another processor, and apps associated with non-critical nodes are assigned to run on a third processor.

The Amulet is assembled within a wearable device. In an embodiment, the Amulet is assembled into a bracelet or anklet, or a module attached to a bracelet or anklet, for attachment to a limb of a patient.

In use, the Amulet 100 (FIG. 2) is attached to a patient and, when the patient's separate Bluetooth-enabled smart cell phone 202 is within range of the Amulet, may periodically communicate data to cell phone 202. The cell phone 202 may process, store, or display the data to the patient. In certain applications, the cell phone 202 may also upload some or all of the data received from the Amulet, or a summary thereof, through the Internet 204 to a prescription and medical records server 206. In an alternative embodiment, the cell phone 202 may aggregate the data with data received from other devices prior to, or during, uploading to the server 206. Communications with server 206 are not continuous in order to conserve power at both the cell phone 202 and the Amulet; they are typically initiated according to a previously-configured schedule recorded in the Amulet or cell phone, or when an emergency situation is detected by the Amulet or cell phone.

In an embodiment, the Amulet detects an emergency situation when any one or more of the following events occurs: a) an emergency key sequence is pressed on keyboard 118, b) an associated node detects a loss of pulse, or a pulse, blood pressure, or electrocardiogram outside established limits for rate or quality—such as an onset of fibrillation, c) or an app running on the Amulet determines that an emergency exists from other sensor data provided by associated nodes.

A mini-USB connector (not shown) is provided on the Amulet for coupling external USB master devices to USB-port interface 112 of Amulet 100. A medical practitioner or emergency personnel may attach a laptop computer to the mini-USB connector; when the Amulet determines that security protocols are satisfied, the Amulet provides a patient identification and allows the practitioner or emergency personnel to read any medical records stored within a flash memory 130 of the device. In an embodiment, emergency personnel are restricted to reading only those records designated as accessible to emergency personnel. In some embodiments, once the Amulet determines that security protocols are satisfied, including a correct patient identification and passwords, the Amulet may permit a practitioner to enter configuration information for the Amulet and/or any sensor and/or actuator nodes the Amulet may be in communication with.

To conserve memory, to permit operation with later-developed sensor and/or actuator nodes, and to provide maximum flexibility of the system, the Amulet has an electrically erasable and reprogrammable (FLASH) memory 132 for storing a summary medical record for emergency use, as well as device-specific application code, and device configuration information, applicable to the specific devices assigned to or prescribed to the patient.

Sensors and Actuators Operable with the Amulet

Only rarely would the Amulet be prescribed to a patient for operation independently, without other nodes associated with it. In most embodiments, the patient would obtain (or be provided) other devices for monitoring and managing his or her health. Such devices may be implanted in the patient, worn or carried by the patient, or used intermittently as needed.

The processor of the Amulet uses its body-area-network radio 124 to periodically interrogate one or more sensor and/or actuator nodes 210, 211, 212, 214, 216, 218, 220, 222, 224, 226 that it has been configured to operate with in a body-area network. The Amulet serves as a greatly enhanced BCU. These sensor and/or actuator nodes may be selected from a large number of compatible devices. Each periodic interrogation has a data reading phase, and may also have a configuration command phase. During each interrogation, Amulet 100 uses its BAN radio 124 to poll for, and receive data from, each sensor and/or actuator node 210-226. This data is buffered within the Amulet's memory 108. Upon communication with the cell phone 202, this data is copied to the cell phone 202 or through the cell phone to the server 206. Copied data is then retained in the Amulet for a remainder of a prescribed data-retention interval, eventually being erased to make room for new data from the nodes. The Amulet may, depending upon specific machine-readable instructions in a downloadable app associated with the nodes, process and/or summarize the received data, and may determine if an alarm condition exists prior to uploading the data to cell phone and/or server. Amulet therefore acts as a store-and-forward BAN controller with processing capability configurable by apps appropriate to the nodes and automatically downloaded from a server, where each app includes specific machine-readable instructions for processing data associated with particular nodes, for storing and forwarding that data, and for determining what, if any, data summaries or data for uploading to the cell phone and/or server.

In an alternative embodiment, the Amulet acts as a BAN controller, and may store and forward data from some nodes, but instructs one or more other nodes to transmit their data directly to the cell phone 202 or server, or to other nodes of the BAN at particular times. In this alternative embodiment, the Amulet need not have storage space to buffer all collected data until that data can be forwarded to the cell phone or server.

While a polling model for BAN communications is described in the preceding paragraph, alternative embodiments of the Amulet operate with other network models. For example, an alternative embodiment may operate the BAN using an assigned time slot for each node to transmit data, and in another embodiment a carrier-sense, multiple-access, collision-detect (CSMA-CD) networking model.

Implantable Nodes

Implantable devices are known that combine one or more sensors and one or more electronic or electromechanical actuators. Examples devices include pacemakers 210 as used for treating heart arrhythmias including second- or third-degree heart block, and deep neural stimulators (not shown) such as may be used for treating Parkinson's disease. Some such devices marketed today are equipped with a wireless, transcutaneous communications system that may be used to read critical sensor data, operational data, and battery status. Many pacemakers and deep neural stimulators are also configurable by a physician through a programming device that communicates transdermally with the implantable device. An implantable pacemaker 210 or deep-neural stimulator may be configured with a digital radio for communication with the Amulet; and to receive configuration information from, and provide data such as heart rates, battery levels, and recorded episodes of arrhythmia, to the Amulet. Each such implantable device is assigned an individual device serial number, and the Amulet recognizes the implantable devices as belonging to the assigned patient and to its body-area network by serial number.

Wearable Nodes

Some other electronic devices with electromechanical actuators are worn on the body, including insulin pumps 212. Typical insulin pumps for use in treating diabetes have an electronics node with an electromechanical pump worn on a patient's belt, the electromechanical pump being coupled through tubing to a transdermal needle inserted through, and taped to, the patient's skin. Future models may incorporate glucose sensors, and implantable versions—the long-sought artificial pancreas—may arrive on the market. Insulin pumps are typically also configurable to provide proper insulin dosage, and may have sensors, such as push-button switches and microphones, to permit tactile or verbal wearer input—such as input for advising the electronics of the insulin pump of mealtime.

In an embodiment, a modified insulin pump node 300 for use with the Amulet has a battery, a capacitor for retaining memory information while the battery is being changed, and low-battery sensor 302; this communicates over a local bus 304 with a processor 306 having firmware and RAM memories 308, the processor 306 also uses bus 304 to communicate with other blocks of the insulin pump node. Other blocks of the node 300 include a low-powered digital radio 310 for communication with the Amulet and an accelerometer and gyro 312. Together, the battery, capacitor, and battery sensor 302, processor 306, bus 304, firmware memory and RAM memory 310, and accelerometer 312 form a common core 314 that may be adapted to other nodes useable with the Amulet. Typically, firmware memory 310 has one or more of a read-only memory ROM, programmable read-only memory PROM, or erasable and reprogrammable read-only memory (EEPROM) including machine-readable firmware instructions for instructing processor 306 to perform basic operation and configuration of the node, and typically further includes node type and serial-number identification for the node in machine-readable form.

In the insulin pump node 300, the bus 304 of common core 314 also permits processor 306 to communicate with insulin-pump specific components 313 including a display 316, a small keyboard 318 through which the patient may enter status changes such as mealtime indications, a level indicator of an insulin reservoir 320, and an electromechanical pump 322 that is coupled to draw insulin from reservoir and pump the insulin through a tube to an injector needle 324. In some embodiments, bus 304 also permits processor 306 to communicate with a glucose sensor 326. Processor 306 has firmware for using radio 310 to receive configuration information from, and providing data such as remaining insulin levels, glucose levels, and recorded wearer inputs to, the Amulet.

Moderate pain may be treated by transdermal electrical stimulation (TENS), and severe pain may be treated by drugs injected by either the subcutaneous or epidural routes from a wearable pump. Patient-controlled analgesic pumps (PCA) for delivery of pain control medications are known in the medical art, although many available today are not wearable. Wearable pain treatment pumps require configuration with appropriate dosage information, and may provide data such as remaining drug and battery charge levels. Similarly TENS units also require proper electrode placement and configuration; TENS units may provide data such as battery charge and skin continuity and conductivity data.

Pain pumps 214 and TENS units 218 may be constructed around common core 314, with appropriate firmware and specific hardware that may differ from the specific components 313 of the insulin pump.

Some injectable chemotherapy agents, both for cancer therapy and some other therapies, may also be adaptable for administration through a wearable pump, potentially coupled to a peripheral-into-central-vein (PIC) catheter or other central venous port; these pumps when used with the Amulet may permit administration of these therapies in an outpatient setting instead of in an inpatient setting. Wearable chemotherapy pumps require configuration with appropriate dosage information, and may provide data such as remaining chemotherapy agent levels and battery charge levels. Chemotherapy pumps 216 may be constructed around common core 314, with appropriate firmware and specific hardware that may differ from the specific components 313 of the insulin pump.

Hearing aids have become common; these are typically worn on the body. Cochlear implants are also frequently used, usually in combination with a microphone, processing, and configuration device attached to, but not implanted in, the patient's body. Both of these types of hearing-assistance devices 220 are typically configurable, permitting adjustment of gain, frequency response, and, for cochlear implants, a mapping of frequency to stimulus electrodes. Hearing assistance devices 220 may be constructed around common core 314, with appropriate firmware and specific hardware that differs from the specific components 313 of the insulin pump.

Other types of prosthetic devices are also known, including myoelectric limbs; since diabetes is a leading cause of amputations, these devices are more frequently worn by patients needing insulin pumps than by the general public. These prosthetics may in some instances be configurable with adjustable gain and thresholds, and have batteries that may become discharged or fail. Prosthetic devices 222 may be constructed around common core 314, with appropriate firmware and specific hardware that adjusts sensor thresholds and monitors battery levels as well as directing operation of motors coupled to joints and terminal devices of the prosthetic device.

Similarly, muscle or bone-healing stimulator devices 224 are typically configurable, permitting adjustment of stimulus levels and stimulus timing. Stimulator devices 220 may be constructed around common core 314, with appropriate firmware and specific hardware for stimulating muscles or bone growth.

Similarly, temporary pacemakers worn outside the body and communicating with the heart through a transcutaneous wire are known, and are typically configurable, permitting adjustment of stimulus levels and stimulus timing. Temporary pacemakers may be constructed around common core 314, with appropriate firmware and specific hardware for stimulating cardiac contractions.

Similarly, cardiac monitors 211 worn outside the body and sensing cardiac activity through skin electrodes are known. Cardiac monitors 211 may be constructed around common core 314, with appropriate firmware and specific hardware for detecting problems and sounding alarms; alarms may also be transmitted to the Amulet and thence to the server 206 for alerting emergency medical personnel.

Some patients, including elderly individuals afflicted with Alzheimer's disease, may wander. Similarly, sex offenders being treated with testosterone-depleting medications through a wearable pump may have travel restrictions imposed on them as part of probation. Either the Amulet 100, an associated cell phone 202, or a separate node built around common core 314, may be equipped with a global positioning satellite (GPS) device permitting the Amulet to determine patient location and to transmit that location to the server 206 to permit attendants to locate the patient.

Many obese patients, or patients undergoing rehabilitation, may need encouragement of activity, and it may be desirable to track their physical activity. A node built around common core 314, may be provided with an accelerometer to serve as a pedometer, or other sensors for monitoring physical activity. This activity information may be transmitted to the server 206 to permit physician monitoring of patient activity.

Some patients may require intravenous or enteral feeding through a PEG tube or nasogastric tube. A node built around common core 314, may be provided with a feeding pump and reservoir that may be configured according to a feeding prescription. A patient may carry this pump and reservoir in a small backpack while conducting other activities.

It is known that some people have a fear of medical personnel that causes their blood pressure to rise when their blood pressure is taken by medical personnel, possibly provoking needless treatment for hypertension. In established hypertension patients, especially those who are poorly controlled, it can be desirable to monitor treatment effectiveness regularly. These patients may wear an automatic blood-pressure cuff, or may be instructed to apply such a cuff at particular intervals. Patients in an intensive care unit may have catheters inserted into arteries permitting direct measurement of blood pressure. A node built around common core 314, may be equipped with an automatic blood-pressure cuff or other blood-pressure sensor for providing the Amulet with blood-pressure information that may be transmitted to the server 206 to permit blood-pressure monitoring of patients.

Yet more devices that could be adapted for use with the Amulet may become available in the future, including wearable or potentially implantable visual prosthetics, and sensors for measuring platelet counts and other blood parameters of chemotherapy patients; the list of devices herein is not intended to be exhaustive.

Encountered or Temporary Devices

The Amulet may also recognize and be useful to record patient use and performance on additional temporary devices that are not continually attached to the patient. Such temporary devices 216 may include exercise equipment in a physical therapy treatment room, scales for determining patient weight, vital signs (including temperature and blood pressure) recording devices, pill boxes and other medication dispensing devices, even imaging devices and patient identification devices. Each of these devices may incorporate elements of common core 314. To verify that data from these devices is associated with the correct patient, in some embodiments, these devices may associate with, and transmit data to, the Amulet using an alternative verification process described below.

Many obese patients, or grossly underweight patients, may require weight be recorded periodically. A node built around common core 314, may be provided with scale. Patient weight information may be transmitted to the server 206 by a temporary node.

Security

Some sensor and actuator nodes 210-224 as described above may provide drugs or stimuli that are hazardous to the patient if they are misconfigured with parameters intended for another patient, when legitimate commands are spoofed by malicious people or electronics, or when attached to the wrong patient. It is also desirable to ensure the Amulet records data from, and provides commands to, only nodes prescribed to and in use by the patient wearing the Amulet, while ignoring or refusing to communicate with nodes attached to other patients. Further, patients generally desire that their emergency summary medical records and data recorded by their sensor and actuator nodes be provided only to their preferred medical providers, and not to unauthorized third parties.

To ensure privacy of patient data, to preserve the confidentiality, authenticity, and integrity of configuration commands, to prevent inadvertent interference by misinterpreting communications from another patient's Amulet as commands to devices of the patient, and similar problems, or other miscommunications once a node 210-214 has been recognized by the Amulet and configured for operation on its BAN, communications between the Amulet 100 and the nodes 210-224 are encrypted using a shared encryption key generated by the Amulet and transmitted to the node at the time that node is configured, and recorded in memory of the node. Further, each configuration communication transmitted by the Amulet to a node has a sequence number or a timestamp encrypted along with the data to prevent forgery or replay, or other spoofing, by an adversarial party nearby; similarly, each data communication from a node to the Amulet has a sequence number to prevent forgery or replay by an adversary. In an alternative embodiment, each data communication to or from a node has a message authentication code to prevent forgery, reply, or spoofing, where the message authentication code is an encrypted hash function of both the data and a timestamp or sequence number. Further, communications between the Amulet and prescription and records server 206 are also encrypted using methods conventional for Internet communications.

It is desirable to ensure that the Amulet reports information from, and sends commands to, nodes that are actually on the patient the Amulet is associated with, and not attached to some other person or patient; this is particularly important with nodes that are worn exterior to the patient's body and not implanted in the patient. The Amulet ignores nodes on other patients that are not previously associated with it. The Amulet reports as erroneous data from nodes associated with it that are located on a different patient. To determine whether the Amulet is on the same person or patient, each node having common core 314, has motion sensors incorporating an accelerometer, and in some embodiments an optional gyro 312. The node transmits readings from the motion sensors to the Amulet, both on activation and attachment to a patient, and periodically thereafter, transmits measurements from the motion sensors including accelerometers 312 to Amulet 100, where processor 106 performs a smoothing algorithm on the readings from both the node's and the Amulet's accelerometers.

In an embodiment, motion sensors of Amulet 126 and common core 314 include accelerometers 312 in three axes, such that a squared sum of readings of the accelerometers represents the gravitational force on the node or Amulet and accelerations induced by significant subject motions such as walking. The processor then correlates the accelerometer readings by performing a coherence determination in a manner similar to that described in Cornelius and Kotz. The coherence determination effectively uses accelerations associated with each walking step to identify nodes as attached to the same individual when those walking steps are fully synchronized for a period of time and are consistent with the Amulet being on the same body as each node.

Data from the motion sensors, including accelerometers 126, of the Amulet are analyzed to detect periods when the subject or patient wearing the Amulet is walking or running; walking or running will typically produce a rhythmic acceleration having recognizable characteristics.

Once the subject or patient wearing the Amulet is walking, sensor data recorded during corresponding, non-overlapping, time intervals from motion sensors of the common core 314, including accelerometers 312, and motion sensors, including accelerometers 126, of the Amulet are analyzed. This analysis includes first determining a magnitude by summing squares of accelerations in all three axes monitored by each accelerometer. A feature vector is then computed for each of the Amulet and node accelerometer including a mean, standard deviation, variance, mean absolute deviation, interquartile range, power, and energy.

Coherence is a measure of how well two signals correlate in the frequency domain. More precisely, it is the cross-spectral density of two signals divided by the autospectral density of each individual signal. We approximate coherence using the magnitude-squared coherence:

$$C_{XY}(\varphi) = \frac{[S_{XY}(\varphi)]^2}{S_{xy}(\varphi)S_{yy}(\varphi)}$$

In the above, x and y are the signals, $S_{xy}$ is the cross-spectral density between signals x and y, $S_{xx}$ is the autospectral density of signal x, and $\phi$ is the desired frequency.

Cross-spectral density is calculated by the Fourier transform of the cross-correlation function. If x and y are well correlated at some frequency $\phi$, then $C_{xy}(\phi)$ is close to 1.

To get a final measure over many frequencies, we compute the normalized magnitude-squared coherence up to a frequency $\phi_{max}$ of 10 hertz:

$$N(x; y) = \frac{1}{\varphi_{max}} \int_0^{\varphi_{max}} C_{xy}(\varphi) \, d\varphi$$

Given two sets of feature matrices A=(F1; F2; : : : ) and B=(F1; F2; : : : ) with entries Fj as described above, we want to determine how well A and B are correlated. Here, A and B represent the feature matrices extracted from the accelerometer data of the mobile node and sensor node respectively.

We apply coherence to the feature matrices in the following manner. For some window length c (the feature coherence window), we compute the normalized coherence of A and B as such:

$$N_k^{AB} = \{N(A_{k \ldots k+c}^1, B_{k \ldots k+c}^1), N(A_{k \ldots k+c}^2, B_{k \ldots k+c}^2), N(A_{k \ldots k+c}^7, B_{k \ldots k+c}^7)\}$$

where $A_{k \ldots k+c}^1 = \{f_N^1 \in A : k \leq N < k+c\}$ the window of a specific feature of A.

That is, we take each feature (i.e., a column of the matrix) of A and the corresponding feature of B, and compute the normalized coherence using c samples (i.e., the rows of the matrix). At this stage, we are left with a matrix of normalized coherences for each feature and window k. Because we want to capture how the two signals are related over time, the coherence window c should be sufficiently large to capture periodicities in the features. Because the typical walk cycle is on the order of seconds, we choose a coherence window on the order of several seconds.

To account for the many positions a sensor node might be placed on the body, we collect data from several locations on several walking individuals, and use those data to train a classifier. Once trained, the same classifier model may be used on many production systems.

Given a set of feature coherences and their respective labels, we can train a classifier to learn a model that is the coherence threshold for each feature. We employ a support vector machine (SVM) for this task since, once trained, they are good at predicting which label a given feature coherence is associated with. An SVM accomplishes this task by finding the hyperplane with the largest separation between the set of training feature coherences that are on the same body and those that are not on the same body.

In our experiments, we trained a SVM with a radial basis kernel using LIBSVM, and data sets acquired from sensors located at several different locations on several different subjects.

Given a trained SVM, we can use it to classify whether a given feature coherence is on the same body. That is, at the window the feature coherence was computed, the support vector machine can determine if the sensor node is on the same body as the mobile node. The SVM does so by determining on which side of the hyperplane the test feature coherence lies. While we have shown that accelerometers alone have a high degree of accuracy in confirming that Amulet and node are indeed attached to the same body, it is expected that accuracy can be improved by additionally incorporating gyroscopes (gyros) in the Amulet and each node. Inertial navigation systems typically combine accelerometers in three dimensions with gyros to determine the current position of the system, a process known as dead reckoning. In an alternative embodiment, each node, including the Amulet, has gyros in addition to accelerometers; it is expected that no two patients (or subjects) will navigate in exactly the same manner for an extended period of time.

In an alternative embodiment, where the Amulet has a pulse sensor, such as a sensitive pulse oximeter capable of monitoring a wearing subject's pulse, readings from pulse sensors of other nodes, which may include electrocardiographic pulse sensors, blood pressure cuff pressure-wave, and Korotkof-sound pulse sensors as well as pulse-oximeter sensors, are correlated to the pulse sensor of the Amulet to identify nodes as attached to the same individual as the Amulet. It is expected that only rarely will multiple patients within BAN radio range of each other have precisely synchronized pulses for an extended period of time.

Upon detection of discrepancies between accelerometer readings indicating that the node and Amulet are on different people, the Amulet marks data relayed from those nodes to server 206 as suspect and, for nodes subject to abuse (such as patient-controlled pain pumps) may suspend operation of particular nodes. Similarly, whenever the Amulet detects, through additional sensors 130, that it is not in contact with a patient, or detects significant differences between readings from those sensors and duplicate or complimentary sensors in other nodes, it similarly sounds an alarm and restricts function.

Where particular nodes provide data that can be correlated to data from other sensors or sensors in the Amulet, such as a cardiac monitor or blood-pressure node whose pulse readings for rate, rhythm, and timing can be compared to pulse information derived from the Amulet's pulse meter 114, the Amulet uses these additional readings to verify that it and the Amulet are indeed attached to the same body. In an alternative embodiment, the Amulet directly correlates pulse beats as detected by the optional pulse sensor 114 in the Amulet to pulse beats as detected by pulse sensors in the other node. For example, in some embodiments wherein the Amulet includes a pulse meter, if that pulse meter detects pulse characteristics, such as pulse rate, that are inconsistent with readings obtained from a cardiac monitor 211, or from a pulse meter in a chemotherapy pump 216 or pain pump 214, it may similarly alarm and restrict function. In an embodiment, the Amulet's pulse meter is a sensitive pulse oximeter that can measure heartbeats and respirations by sensing minute changes in blood oxygenation.

In an alternative embodiment, instead of presuming that the Amulet is worn by a correct patient and validating the nodes as being on the same patient as the Amulet, the Amulet identifies its wearer from a list of preconfigured permitted wearers using an optional fingerprint sensor 128.

In an alternative embodiment, instead of presuming that the Amulet is worn by a correct patient and validating the nodes as being on the same patient as the Amulet, the Amulet identifies its wearer by communication with an implanted node having a serial number that identifies the wearer, and then validating its sensor data as consistent with data from the implanted node.

In an alternative embodiment, at least one of the wearable nodes, which may be, but need not be, the Amulet node, contains a body-contact microphone 129. By collecting voice samples from the microphone of this node, our method allows the device to determine whether (a) the speaker is indeed the expected person, and (b) the microphone device is physically on the speaker's body. Transitively, using the methods described above using accelerometers (and optional gyroscopes), the Amulet can determine that it is on the same body as the microphone device and thus is itself on the expected person.

In another alternative embodiment, the Amulet includes a microphone, and one or more of the other wearable nodes also includes a microphone, or two or more nodes include microphones. Correlation of these microphones' signals can be used to determine whether the Amulet and devices are on the same body.

In the alternative embodiment with a microphone-equipped node or nodes, and in the alternative embodiments having an Amulet with a microphone, the processor 106 of the Amulet determines when the wearer is speaking. When the wearer is speaking, the processor 106 then determines Mel-Frequency Cepstral Coefficients (MFCCs) of twenty millisecond intervals of data from the microphone of each node or Amulet having a microphone. The MFCCs are coefficients that describe the power spectrum of logarithm of the power spectrum when mapped to the Mel scale, which is empirically related to the frequency characteristics of the human ear. In addition to these coefficients, we include the first and second derivatives (velocity and acceleration) of each coefficient, to capture how the coefficients change over time. Each derivative is approximated from a 5-point central difference:

$$v_t^{(1)} = \frac{c_{t-2}^{(1)} - 8c_{t-1}^{(1)} + 8c_{t+1}^{(1)} - c_{t+2}^{(1)}}{12}$$

Where $V_t^{(1)}$ is the velocity of the first coefficient $c_t^{(1)}$ at time t. This provides a feature vector for each audio segment for a chosen number of coefficients.

The feature vectors are then statistically modeled using a Gaussian Mixture Model (GMM) of training MFCCs is then derived, and MFCCs are classified using a classifier and GMMs from data recorded by the Amulet determine if the data is consistent with at least one entry of a small database in the Amulet to determine subject identity, and finally with GMMs from data recorded by other nodes to determine if they are on the same body. In an embodiment, the small database in the Amulet has GMMs derived from recorded voice of a subject to which the Amulet is prescribed, as well as GMMs derived from recorded voice of other members of the subject's household, as well as a selection of other people, such as caregivers and medical personnel like nurses that the subject is reasonably expected to be in contact with frequently.

Experiments have been conducted using data recorded by one or both a contact microphone and an air microphone, as reported in Cornelius, et al. These experiments show that, using a contact microphone with the MFCC feature extraction and GMMs herein described, a processor can often identify which of several possible wearers is the subject wearing the microphone. Experiment also shows that, if microphones are placed on the body in appropriate locations, a processor can also often distinguish between audio recorded on a subject that is speaking and audio recorded by a microphone worn by a nearby person through air transmission.

It is expected that alternative embodiments may use the MFCC feature extraction and GMMs herein described, or alternative vocal features, methods of feature extraction, statistical models of features, and classifiers to both identify an individual wearing subject and/or to verify that two or more microphone-equipped devices are worn by a same subject.

In an alternative embodiment having a microphone-equipped device at least one such device contains speech recognition configuration files trained to a specific wearer, or a library of such speech recognition configuration files each trained to a specific wearer of a small number of potential wearers.

Figure 5:
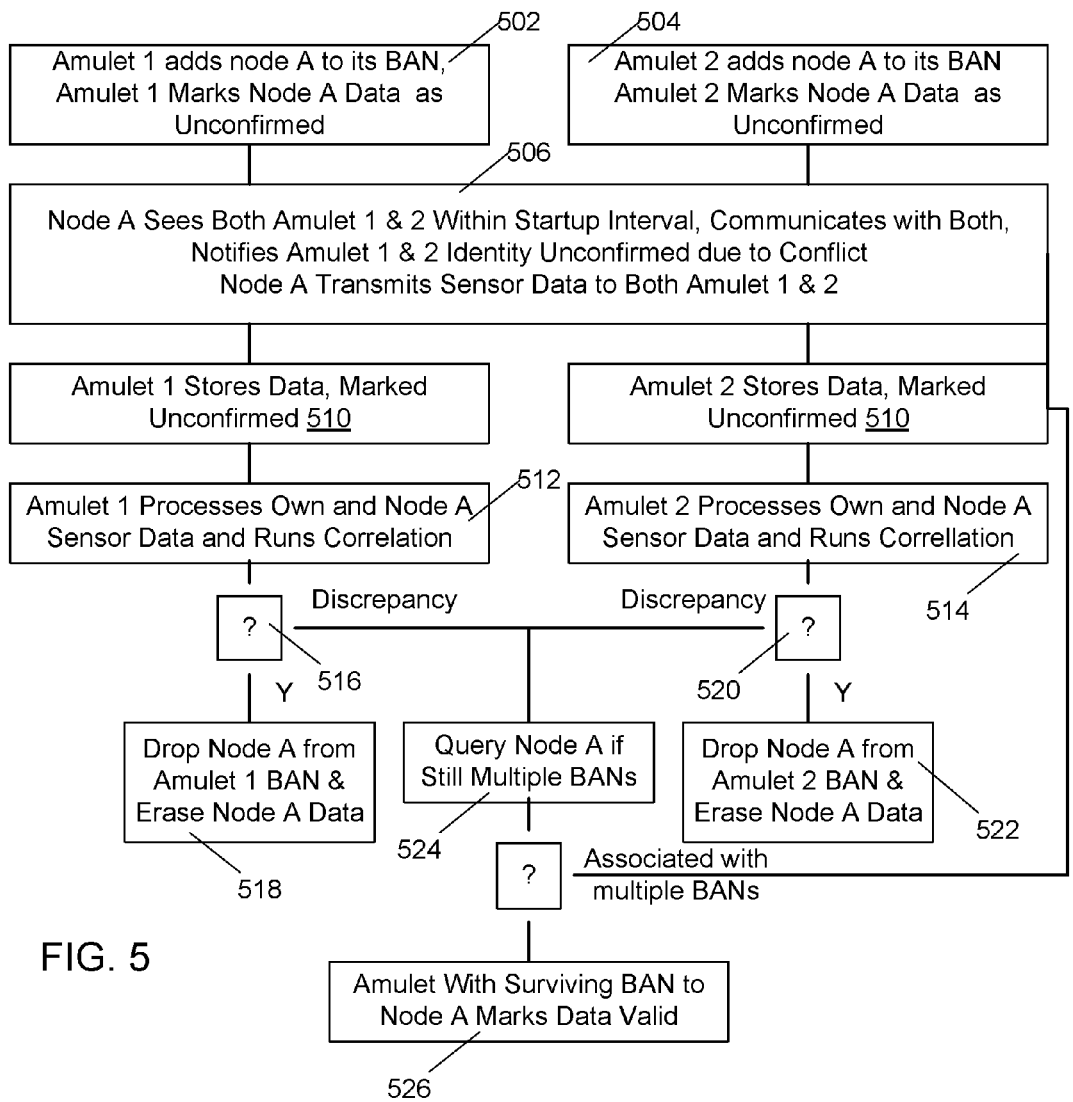
FIG. 5 is a flowchart of a method of determining which Amulet and BAN should associate with a newly turned-on node attached to a body.

Consider a case when a husband and wife share a bathroom while dressing, then move about a house independently, and where each of husband and wife wear an Amulet and one or more sensor nodes—but accidentally swap sensor nodes. In an alternative embodiment illustrated in FIG. 5, where two or more Amulets and several nodes are within BAN radio range of each other within a startup interval of turning on the nodes and attachment to a person, each node may initially be added to two or more BANs associated with two or more Amulets, where each BAN is associated with a single Amulet, and the nodes communicate with the Amulets using encrypted communications. In the two Amulet case, a first Amulet adds 502 node A to its BAN, and a second Amulet adds 504 node A to its BAN. Both Amulets mark data as associated with a person of unconfirmed identity.

Since each node in communication with two or more Amulets has separate encryption keys associated with each Amulet, they are aware they are communicating with two or more Amulets. Node A therefore also flags 506 the data it transmits as belonging to a person of unconfirmed identity because it is communicating with more than one Amulet. Node A transmits data to both Amulets from both its primary sensors, such as glucose sensor 326, and from any auxiliary sensors provided for subject confirmation, such as motion sensors including accelerometers 312, microphones, or pulse sensors.

Each Amulet continues to store and mark the data as unconfirmed 510. In the event one of the Amulets goes out of range of node A, the node drops out of the BAN associated with that Amulet, during this association confirmation phase the Amulet assumes that an Amulet going out of range indicates that that particular node is on a different person, and will refuse to re-associate with that node should it come back into range.

Each Amulet then processes its own sensor readings, such as motion sensors including accelerometer 126, pulse meter 114, or microphone 129, and correlates 512, 514 this data against corresponding sensor data from node A.

Typically, sensor data from node A worn by a first person will not correlate with data from sensors in an Amulet worn by a second person. For example, if a subject wearing the Amulet walks, motions associated with walking and detected by the sensors in the Amulet will have differences in timing than motions detected by sensors in node A if node A is worn by a separate person. If 516 discrepancies are detected between sensors of node A and those of the first Amulet, the first Amulet drops 518 node A from its BAN and erases sensor data received from node A. Similarly, if 520 discrepancies are detected between sensors of node A and those of the second Amulet, the second Amulet drops 522 node A from its BAN and erases sensor data received from node A. Periodically each Amulet queries 524 node A if it is still associated with more than one BAN. If node A is still associated with more than one BAN and Amulet, data remains unconfirmed, and additional sensor data is processed and correlated to identify which Amulet is on the same person as node A.

Once Amulets having mismatched correlations drop their BAN connections to node A, and an Amulet has confirmed matching correlation with data from node A, data from node A is marked confirmed 524 in that Amulet, and data from node A will be processed normally.

In an alternative embodiment, after computing GMMs from the MFCCs computed from microphone data of Amulet and any associated nodes, the MFCCs are tested by a classifier 135 to see how well they fit GMMs of a library or database 137 of GMMs associated with persons who are authorized wearers of the Amulet. When a matching GMM is found, the Amulet is assigned to that person. In this way, should husband and wife swap Amulets (whether accidentally or on purpose), the Amulets will be able to recognize the situation because the library or small database of GMMs would typically include GMMs derived from people in the same household. Each of the Amulets will then upload their data to medical records on the server associated with the person actually wearing that Amulet.

Further, in a voice-controlled embodiment, once the Amulet has identified which specific potential wearer has donned the Amulet, the Amulet selects appropriate speech recognition configuration files trained to that specific wearer from its library of speech configuration files, and uses those appropriate files to configure speech recognition routines that execute on the Amulet when the wearer speaks. This embodiment of the Amulet may therefore be voice-controlled with both a greater certainty of correct command recognition and a larger vocabulary of Amulet commands than a voice-controlled device having generic speech recognition configuration files. The Amulet may relay certain commands over the uplink radio 122 to the cell phone, which in an alternative embodiment includes commands for applications, including dialing, text messaging, and web browser applications, running on the cell phone.

Bioimpedance Biometric

In an embodiment, in addition to, or as an alternative to, contact microphone 129 and the method heretofore discussed for using GMMs and MFCs to identify a person or subject wearing the Amulet, one or more of the Amulet or another node of the BAN associated with the Amulet is equipped with a bioimpedance sensor 131.

The sensor 131 measures bioimpedance by applying a small sinusoidal alternating current between a first or stimulus pair of electrodes attached to the skin. The injected current establishes an electrical field within the skin and underlying tissue and results in a measurable voltage difference between the electrodes. Alternatively, a second or sensing pair of electrodes located between, near, or distance from the stimulus pair of electrodes may be used to sense voltage differences due to the electric field in the tissue, automatically ignoring potentially-high skin-contact resistances. This potential difference is measured, and is expected to be a function of the underlying tissue impedance. Specifically, the alternating current (AC) version of Ohm's law, V=IZ, relates the voltage V and current I to the bioimpedance Z of the tissue. Since many tissues exhibit dispersive characteristics, meaning that their electrical properties are dependent on the frequency at which they are measured, the sensor 131 adjusts the frequency of the alternating current over a specific band, recording impedance at each of several frequencies, and permits processor 106 to perform impedance spectroscopy to determine complex impedance. Complex bioimpedance, $Z(\omega)$, combines resistive and reactive components, $Z(\omega)=R(\omega)+jX(\omega)$, where R is the frequency dependent tissue resistance, X is the frequency dependent tissue reactance, $\omega$ is the signal frequency, and j represents the imaginary quantity the square root of −1. These can also be recorded in terms of admittance $Y(\omega)$ which is the reciprocal of $Z(\omega)$.

The anatomy of the forearm proximal to the wrist includes skeletal bones (radius and ulna), arteries, veins, nerves, muscles, adipose, skin, and interstitial fluids. Over the frequency range of 10 kHz to 10 MHz reported values of bone conductivity and adipose conductivity are relatively stable. In muscle, skin, and blood, however, the conductivity monotonically increases with frequency. Person-to-person differences at the wrist include: size, skin thickness, skin water content, bony anatomy and size, vascular branch size and locations, sub-dermal water content, and adipose/muscle/bone/vasculature content within the sensing region. All of these parameters will have an impact on the actual impedance measured at the wrist. An Amulet, or wrist-mounted node worn in a manner similar to that of a wristwatch, is expected to be able to sense these differences.

Since the anatomy of the ankle resembles that of the wrist, it is expected that person-to-person differences similar to those measured at the wrist will be observable by an ankle-mounted Amulet or node and permit that device to sense person-person differences. Some other anatomical locations, such as the neck or chest, may also have sufficient person-to-person differences for a pendant or necklace-mounted Amulet or node to detect and sense person-person differences.

In an alternative embodiment, the Amulet senses bioimpedance between itself and a second node by sourcing an AC voltage signal of some known magnitude between two Amulet-based electrodes. This establishes a potential field that propagates along the skin in a manner that depends on magnitude and frequency of the signal generated and distance along the skin. In another node of the BAN, a sensor picks up the signal on one or more skin electrodes. The change in magnitude between source (Amulet) and sense (Sensor node) can be used to determine if the Amulet and the other node of the BAN are on the same body; this change in magnitude depends on the other node location with respect to the Amulet and the bioimpedance encountered in the wearer by the signal. The impedance between the Amulet and the other node can be used both to determine that both nodes are on the same wearer, and can be used as part of wearer identification.

In a particular embodiment, an 8-electrode bracelet is attached to a wrist-wearable electronic unit. By switching through multiple pairings of electrodes, a list of bioimpedance measurements associated with an individual's wrist can be recorded and ultimately used for recognizing an individual from within a group of individuals. The electronic unit has two modes of operation, an enrollment mode, and a recognition mode. In the enrollment mode, the sensor captures five bioimpedance measurements from the wearer in under a minute. The device uses these training measurements as inputs to an enrollment routine that learns a model of the new wearer, or enrollee's, bioimpedance and enters it into a small database 137 of potential wearers, such as family members and caretakers, in flash memory 132 of the Amulet. In an embodiment, database 137 is updated when an authorizing application connects to the Amulet through USB connector 112 or radio 122 and provides basic identification information of a potential wearer; the Amulet then learns bioimpedance and/or vocal resonance data from that new wearer and records that data with the basic identification information in database 137.

In the recognition mode, the device periodically determines whether it is on a person's body, then if it is on a body it collects bioimpedance measurements and uses a recognition algorithm or classifier 135 to determine whether the enrollee's model matches the measured bioimpedance for a particular wearer in the database 137 of potential wearers. For bi-polar measurements, the Amulet uses those electrodes directly across from one another, for example but not limited to electrodes 1 and 5, since they are the maximal distance away from each other and therefore provide more tissue for the current to travel through. Other bipolar electrode configurations may also function in a device, such as adjacent electrodes. Similarly for tetra-polar measurements, we chose to apply current between those electrodes directly across from each other and measure from the other electrodes that are directly across from each other (i.e., apply 1 and 5, measure between 2 and 6, 3 and 7, and 4 and 8). Other tetrapolar electrode configurations are also possible. We represent these pairs as a compact list where the first two elements are the electrodes applying current and the last two elements are the electrodes measuring bioimpedance.

Given a set of frequencies and their corresponding bioimpedance measurements, processor 106 executes machine readable instructions in memory 108 to extract 7 features from each bioimpedance measurement to form a feature vector. These features include the maximum magnitude of all the bioimpedance measurements. The other six features capture the shape of a plot of the bioimpedance measurements as a whole. We fit a line to the bioimpedance measurements in log-log space, which smooths over the measurements themselves while also preserving the general shape of the curve formed by the measurements. We fit a line for the resistance part, the reactance part, and the magnitude of the bioimpedance measurements. Because each fitted line is succinctly described by a slope and intercept there are six such slope and intercept features. In an alternative embodiment, an impedance curve parameterized with electrical equivalent models, Cole models, or another transfer function that can be modeled and parameters of the models used as identifying features in place of slope and intercept features. Additional or fewer features can also be used. In alternative embodiments, additional features are extracted from the bioimpedance measurements to form the feature vector.

A classifier 135, which in a prototype embodiment is a kNN (k-nearest-neighbors) classifier, and in an alternative prototype embodiment a Naïve Bayes classifier that independently models the mean and variance of each feature assuming a Gaussian distribution; in other embodiments other classifiers may be used. In a particular experiment, in which the Naive Bayes classifier outperformed the kNN classifier, and in which there was little difference in terms of recognition rates between bi-polar and tetra-polar measurements when using a single pattern for bioimpedance recognition, data was obtained from forty-six volunteers and used to test the classifier's ability to discriminate between test subjects. In an embodiment, the impedance measurements were combined with wrist circumference measurements.

In an alternative embodiment, measurements were made of voltages at each electrode using not just one pair of electrodes as stimulus electrodes, but using each of several different selected stimulus electrode pairs of four or more electrodes as stimulus electrodes, thus, if eight electrodes are provided, providing the seven parameters for each stimulus electrode pair. In this embodiment, all extracted parameters from each stimulus electrode pair are used by the classifier to identify a wearer wearing the device from the database 137 of potential wearers.

Prescriptions and Adding Devices to the Amulet BAN

Security protocols are also followed when a device is added to, or removed from, the Amulet's BAN. For example, when adding a node, for example (but not limited to) a pain pump 214, to Amulet 100's network, the prescribing practitioner enters 402 the prescription for the new node into a patient record associated with the Amulet 100 on prescription and records server 206, together with configuration parameters such as dosages.

At the next periodic communication period of Amulet 100, or upon entry of a configuration command to the Amulet, the Amulet communicates 404 through cell phone 202 and network 204 with server 206. When the Amulet finds a new prescription record for the new device, it first verifies the authenticity of the prescription using cryptographic keys and certificates, stored within the Amulet, to verify the cryptographic signature on the prescription. These keys and certificates are stored in tamper-resistant memory within the Amulet. Some certificates are embedded at manufacture time and provide a root of trust for verifying communications from the Amulet manufacturer, other major device manufacturers, and device-certification associations. Other keys and certificates are loaded (through the mini-USB interface) during a visit to the patient's healthcare provider or pharmacist, providing a root of trust for verifying communications with those entities and with the server 206.

If the prescription refers to a device, or refers to an application that may reference one of several devices, for which the Amulet 100 does not yet have an application in FLASH memory 132, the Amulet 100 downloads 406 an application for operation with that device from server 206. The downloaded application is stored in apps 134 portion of FLASH memory 132, together with any associated configuration information 408. In an embodiment Amulet 100 then periodically polls 410 for presence of a device of the new device type. In an alternative embodiment, the subject puts on the node and presses an activation button on a keyboard of the node; the node's BAN radio then begins listening for BAN radios of nearby Amulets. The subject then presses a link button on the keyboard 118 of the Amulet, the Amulet then polls 410 for presence of a new device. When an unconfigured, powered, and enabled, node device is within range and hears a polling Amulet, it responds 412 to the Amulet with its identification and any sensor data it may have. We anticipate that there may be additional alternatives for linking nodes to the Amulet.

The Amulet confirms, through a cryptographic protocol, that the new device is indeed an authentic sensor of the type prescribed. If the sensor data it has, such as accelerometer and gyro data or cardiac pulse data, is consistent 416 with other data available on the Amulet, and hence the new node is on the same body as the Amulet, the associated application in apps 134 runs to associate the Amulet with the node device, transmits any configuration data received from the server and intended for that node, including any specific application code for execution on the node, to the node, and reads the serial number and any initial functional data from the node. The Amulet then creates and sends 414 to the node an encryption key for communications during future normal operations.

During normal operations, the Amulet periodically uses its body-area network radio 124 to poll 418 each node device of the BAN; these devices are each assigned a polling code and address. For stronger privacy guarantees, this protocol may optionally use methods that encrypt the address and other 'header' information. (See, for example, Shrirang Mare, Jacob Sorber, Minho Shin, Cory Cornelius, and David Kotz, "Hide-n-Sense: Privacy-aware secure mHealth sensing", *Technical Report TR*2011-702, Dartmouth College, September 2011.); a similar paper has since been published as Shrirang Mare and Jacob Sorber and Minho Shin and Cory Cornelius and David Kotz. *Hide-n-Sense: preserving privacy efficiently in wireless mHealth.Mobile Networks and Applications (MONET)*, 1-14, June, 2013. Special issue on Wireless Technology for Pervasive Healthcare. DOI 10.1007/s11036-013-0447-x. Each addressed node responds with any sensor data, including battery-level data, it may have available. The associated application within the Amulet processes 420 this data, may store portions of such data for later retrieval by a practitioner or for transmission to the cell phone 202 or server 206, and may provide adjusted configuration information—potentially including (but not limited to) reconfiguring 422 an insulin pump to provide additional insulin at mealtime or to cease operation of a chemotherapy agent infusion pump if a blood parameter node detects out-of-limits blood values—to that node. Periodically the Amulet uses its Bluetooth, or other uplink, radio 122 to poll for the cell phone 202 being in range; if phone 202 is in range, any collected data saved by the application in memory of the Amulet is communicated 424 to the cell phone and, should a cooperating app on the cell phone determine that the data or summary thereof be appropriate for recording on the server, through its network to the server 206.

Temporary Overrides

Same-body identification using accelerometers as heretofore described works best with ambulatory patients; ambulatory patients may have periods when they are bedridden or hospitalized. Similarly, while same-body identification using microphones may be operable with wheelchair-bound patients, these patients may also have periods when they cannot speak.

The prescription database on server 206 therefore has an override flag that, when set by authorized medical personnel, permits operation of the Amulet and nodes of the Amulet's BAN even if the nodes cannot be verified as being on the same body as the Amulet through the accelerometer and vocal resonance methods described above. The override flag is downloaded to the Amulet whenever the Amulet connects through the cell phone to the server. It is expected that this override flag for same-body verification will be set, for example, before a patient is anaesthetized for surgery, and cleared once the patient is ready for ambulation.

In an alternative embodiment, the Amulet has a near-field communications (NFC) radio, such as is used in radio-frequency identification (RFID) tags; in this embodiment, the Amulet is passed adjacent to nodes intended for use on the patient while a configure button is pressed on the Amulet, whereupon the Amulet interrogates an NFC radio in the nodes for node identification and then proceeds to add the nodes to its BAN. The Amulet then assumes that those nodes are on the correct patient so long as the override flag remains set; once the override flag in the database is cleared and downloaded to the Amulet, the Amulet attempts to verify that the nodes are on the same body as each node as previously described.

Node Configuration

Since configuration data intended for a node of a first type to a node of a second, different, type could produce significant problems for a patient wearing the first node, configuration data transmitted by Amulet to a node is secured by including node identification information in a same BAN network packet with the configuration information; the receiving node verifies correctness of the node identification information prior to using the configuration information. In an embodiment, the node identification information is the node type and serial number read by the Amulet when the node is associated with the Amulet and an appropriate app downloaded if necessary and activated on that Amulet.

Encountered or Temporary devices

Consider the possibility of two Amulet wearers undergoing physical therapy on adjacent treadmills in a gym. When associating the Amulet to an encountered device such as a treadmill or medication dispensing device, it is desirable to link particular Amulets to particular devices of the potentially multiple Amulets and multiple encountered devices that may be in range of the BAN radio. Encountered or temporary nodes may also include pulmonary treatment machines, enteral or intravenous feeding pumps, blood-pressure monitors, and other medical equipment that may be attached to a patient for brief operational uses.

During normal operations, the Amulet periodically uses its body-area network radio 124 to poll for presence of a temporary device within a short distance, typically significantly less than the maximum range from Amulet to sensor or actuator modules of the network. When such a device responds to the poll, it includes its type identifier in its response to the Amulet. The Amulet then checks this device type in a table of permitted node types for which it has an associated app. If no associated app is found, the Amulet uses its Bluetooth radio to contact an app and prescription server 206 through cell phone 202 and download an associated app from a server. If the device is permitted, according to a table in the Amulet, the app then executes on processor 106 and adds the temporary device to the Amulet's BAN network. The temporary device will remain associated with the BAN at the full range of Amulet's BAN radio until the device is out of range or the Amulet or device is instructed to drop the link. In some embodiments, a particular app may recognize more than one type of node; and a particular type of node may provide input to more than one type of app. In embodiments, there may be more than one app and prescription server, and the app and prescription servers may, but need not, be separate from a server for logging data reported by the Amulet and apps running on the cell phone.

In an alternative embodiment, an app is authorized in a table on app and prescription server 206 and copied to the Amulet when any node of a type associable with that app is added to the Amulet's BAN. In a particular embodiment, the app may be a general physical therapy tracking app, is authorized by prescription in prescription and app server 206, but the associable nodes include a variety of exercise machine types in a gym.

In the event that the device is not permitted in a device-type authorization table in the Amulet, the Amulet uses its Bluetooth or uplink radio to check for an updated device-type authorization table in server 206. Server 206 therefore maintains master prescription information for devices associable with the Amulet's BAN.

In an alternative embodiment, a new node, or temporary device, uses its BAN radio to listen for a quiet period when neither the Amulet nor any node of the Amulet's BAN is transmitting; the new device then transmits its type identifier to the Amulet during this quiet period. The Amulet may then assign the new node to its BAN, check for an associated app in memory, and, if no app is found, use its Bluetooth or uplink radio to request an appropriate app from server 206.

In an alternative embodiment, the Amulet 100 may include a Near-Field Communication (NFC) radio, which when brought close to a new node (typically, within a few centimeters) will read identity and configuration information from that node. The Amulet may then use its BAN 124 to initiate further communication with the new node; as above, it may assign the new node to its BAN, check for an associated app, and download the appropriate app if necessary.

In an alternative embodiment, instead of limiting recognition of encountered or temporary devices to a short-range BAN-radio mode, these devices are only recognized when a particular key on Amulet keyboard 118 is pressed at the same time as a key on the device is pressed. In this embodiment, verification of prescription and provision of an app where no app is found is performed as described above.

Unlike nodes intended to be worn by the patient, temporary devices revert to an enabled, power-on state wherein they will respond to, and associate with, other Amulets once the link with a particular Amulet is broken. A particular treadmill or exercise bicycle may therefore be used by a sequence of patients each having Amulets without the treadmill being manually reset.

Once a temporary device is added to the Amulet's BAN network, the associated app records data from the temporary device in memory of the Amulet, this data is periodically forwarded to the cell phone 202 and, depending on an associated app in the cell phone, optionally through the phone to the server 206 in a store-and-forward manner along with data collected from other sensors. In alternative embodiments, the cell phone is adapted to display data to the patient or to medical personnel in original, aggregated, or summarized form.

Patient Identification

The Amulet may be interrogated by a pharmacist or clinician (such as nurse or physician) using a device equipped with a Bluetooth or other similar short-range radio to verify patient identity prior to procedures, including surgery, drug refills, or drug administration. This interrogation is protected by a cryptographic protocol to ensure that only authorized entities can obtain or verify the patient's identity. While doing so, the Amulet will provide an error flag if accelerometer or other data received from any node of the BAN is inconsistent with similar data from the Amulet's sensors, thereby warning providers of possible wear by an impostor, or other patient misidentification issues. In embodiments having a fingerprint sensor 128, patient identity is confirmed after the patient swipes a finger over the fingerprint sensor 128.

In an alternative embodiment, the Amulet has a near-field communications (NFC) radio, such as is used in radio-frequency identification (RFID) tags. In this embodiment, the Amulet responds to interrogation of its NFC radio with a patient identifier. In this embodiment, a clinician interrogates the Amulet with an identity verification device prior to performing procedures on the patient.

In an embodiment, the Amulet has a clasp mechanism used to attach the Amulet to the patient. This clasp mechanism includes a sensor that signal the Amulet when it is clasped or unclasped, allowing the Amulet to know when it is attached to a patient or removed from a patient. The Amulet can thereby make more efficient use of the above-mentioned methods for determining patient identity, because it is only necessary to conduct such operation when it is first clasped to a patient.

Patient Records Access

To provide secure access to patient data by medical providers, the Amulet permits access to patient emergency summary and recorded sensor data through the USB port only when it is attached to a patient, as indicated to the processor 106 by built-in sensors such as the pulse meter 114, which in an embodiment is a sensitive pulse oximeter capable of providing both blood oxygenation and pulse information, and other sensors 130. In embodiments having a fingerprint sensor 128, this data is available only after the patient swipes a finger over the fingerprint sensor 128. The need for physical access ensures that the patient will be aware of (and presumably agree to) this emergency access to his or her information, and the requirement that the device sense the patient's presence ensures that the information cannot be accessed when the device is not with the patient.

In a specific embodiment, the Amulet 100 may include a tamper-evident physical mechanism that allows access to the emergency summary and recorded sensor data through the USB port even if the built-in sensors do not confirm the Amulet's presence on the patient. This mechanism may be necessary in certain emergency situations where, for example, the patient has no pulse. Any access via this mechanism requires a physically noticeable change to the Amulet, such as (but not limited to) breaking a seal, such that its use would be noticeable to the patient if misused.

In an embodiment, the Amulet provides a standard file-system interface readable through its USB port and stores content in a common file format such as text format or PDF; thus, the Amulet appears to be a "thumb drive" and at least some data recorded thereon can be viewed on common laptops and similar devices. In a particular embodiment, the Amulet stores and periodically updates data in a format determined by electronic healthcare records standards. In a particular embodiment, the data is formatted according to Consolidated CDA and formatted according to the Cross-Enterprise Document Media Interchange (XDM) standard, making a richer display possible.

Wearer-Identifying Stand-Alone Wearable Devices

Figure 6:
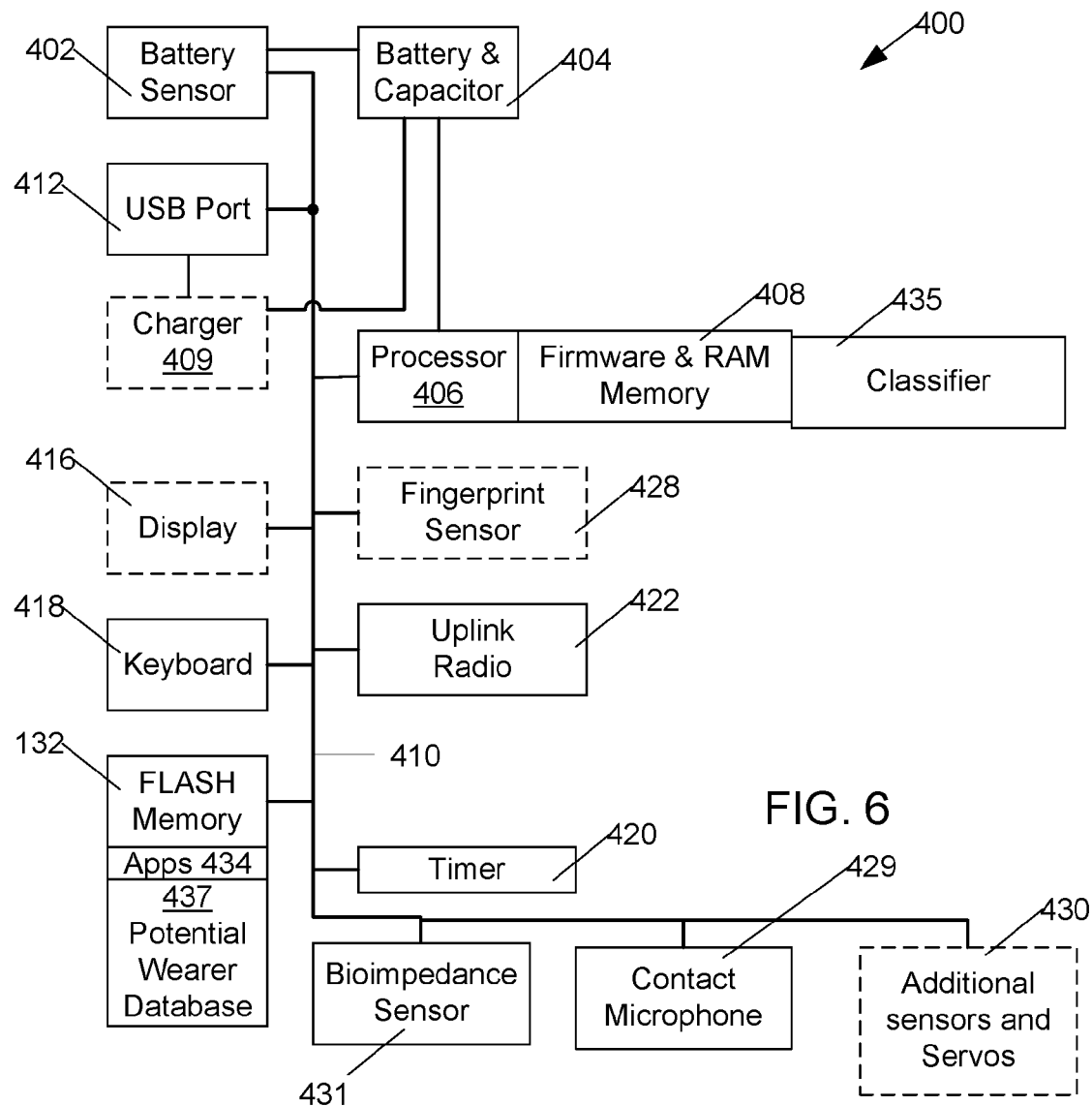
FIG. 6 is a block diagram of a BAN-less wearer-identifying device.

While the Amulet and nodes have been described above in the context of a body area network having ability to verify that its nodes and Amulet are worn by the same wearer, and to identify that wearer, stand-alone wearable devices 400 (FIG. 6) capable of identifying a wearing wearer are useful without the BAN.

Wearable device 400 has a battery voltage sensor 402, a battery 404 for powering the device, a small, low-power, processor 406, and firmware and RAM memory system 408. In an embodiment, a capacitor is provided to retain data in memory 408 while battery 404 is being changed, in an alternative embodiment a USB-powered battery charger 409 is provided for charging rechargeable battery 404. Processor 406 communicates over a bus 410 with battery sensor 402, as well as an optional USB-port interface 412, an optional small liquid-crystal display 416, a tiny keyboard with a few specific-function keys 418, and a clock-timer circuit 420. Processor 406 also communicates with a Bluetooth or other low-powered uplink digital radio 422 transceiver. In an embodiment, the device has an optional fingerprint sensor 428. Additional sensors and actuators 430 may also be optionally included within the device, such as blood glucose sensors, insulin pumps, heart monitors, or other devices. In some embodiments, a bioimpedance sensing device 431 is included in the device; in some embodiments a contact microphone 429 is included in the device; in some embodiments both bioimpedance sensing device 431 and contact microphone 429 are included in the device to provide additional confirmation of wearer identity.

The device has a classifier 435 in firmware memory 408 configured to receive audio data from contact microphone 429, to derive GMMs as described above, and to test these GMMs for fit to GMMs of a library or database 437 of GMMs associated with persons who are authorized wearers of the device; the database 437 being stored in a flash memory 432. When a matching GMM is found, the device recognizes that it is worn by that person. In this way, should husband and wife swap devices (whether accidentally or on purpose), the devices will be able to recognize the situation because the library or small database of GMMs would typically include GMMs derived from people in the same household.

In an embodiment, in addition to, or as an alternative to, contact microphone 429 and the method heretofore discussed for using GMMs and MFCs to identify a person or subject wearing the device, the device is equipped with a bioimpedance sensor 431.

In embodiments having bioimpedance sensor 431, the sensor 431 measures bioimpedance of a wearer's wrist, ankle, or chest as previously described, and processor 406 executes classifier 435 to identify the wearer. In embodiments having both bioimpedance sensor 431 and microphone 429, both sensors are used by processor 406 to identify wearing wearers with a higher accuracy, or from a larger database, than practical with either sensor alone. If the device is uncertain of its identification of a wearer, or if it is being used for a high-security application, it may indicate uncertainty on display 416 and request a fingerprint swipe on optional fingerprint sensor 428.

Once device 400 has identified its wearer, it may commence operation of additional sensors and actuators 430 in a manner consistent with a prescription and app 434; if device 400 is a wearer-recognizing insulin pump or Holter monitor it begins operation once the wearer is recognized.

In an alternative embodiment, device 400 is an electronic key for a vehicle. Once device 400 recognizes which of several authorized wearers is wearing device 400, and a door-open button of keyboard 418 is pressed, device 400 transmits a wearer-specific identification code to the vehicle using uplink radio 422. The vehicle then unlocks its door, and configures itself for operation by the identified wearer by loading preferred radio selections, adjusting driver's seat positions, and in other ways. In a particular embodiment of a family vehicle, the vehicle configures a global positioning system (GPS) device to periodically record, or transmit to a tracking system, position and wearer identification so that parents may track vehicle use by youthful drivers.

In an alternative embodiment, wearable device 400 is worn by a nurse in a hospital, and transmits an a wearer identification code associated with its wearing wearer to a receiver associated with secure storage of restricted medications; only if the wearer identification code is correct does the secure medication store unlock. Similarly, a wearer identification code may be recognized by, and serve as a wearer-id and password for, a medical records computer or other secured computer; such a device provides biometric verification of logins to the computer. In a particular embodiment, uplink radio 422 is a near-field short-range radio, the device is held by the wearer adjacent to a login pad on the computer to perform an automatic wearer identification and login to the computer.

Combinations

The Amulet, or wearable master electronic device, may be made with many possible combinations of features herein described. In particular, the Amulet may have features as described in the following paragraphs:

A wearable master electronic device designated A including at least one processor with a memory, the processor coupled to a radio subsystem, the radio subsystem further including at least one radio, the radio subsystem configured to provide a body area network (BAN) radio function to communicate with nodes of a BAN and to provide an uplink radio function for communications with a server; the memory further comprising machine-readable instructions capable of directing the processor to communicate through the BAN radio with at least one wearable node to receive data therefrom, and machine-readable instructions capable of directing the processor to communicate through the uplink radio to download specific machine-executable instructions associated with the wearable node and to upload data to a server.

A wearable master electronic device designated AA including the features of the wearable master electronic device designated A and further including at least one sensor, and wherein the memory comprises machine-executable instructions capable of directing the processor to process readings from the at least one sensor and readings from at least a second sensor in the wearable node to determine if the wearable node and the wearable master electronic device are worn by a same subject.

A wearable master electronic device designated AB including the features of the wearable master electronic device designated AA wherein the sensor of the wearable master electronic device used to determine if the wearable master electronic device and the wearable node are worn by the same subject comprises an accelerometer.

A wearable master electronic device designated AC including the features of the wearable master electronic device designated AA or AB wherein the machine-readable instructions capable of directing the processor to process readings from the sensors to determine if the wearable node and wearable master electronic device are worn by the same subject comprise instructions for extracting features from data read from the sensors and deriving coherence of the features.

A wearable master electronic device designated AD including the features of the wearable master electronic device designated AA wherein the sensor of the wearable master electronic device used to determine if the wearable master electronic device and the wearable node are worn by the same subject comprises a pulse sensor.

A wearable master electronic device designated AE including the features of the wearable master electronic device designated AA wherein the sensor of the wearable master electronic device used to determine if the wearable master electronic device and the wearable node are worn by the same subject comprises a microphone.

A wearable master electronic device designated AF including the features of the wearable master electronic device designated AA wherein the sensor of the wearable master electronic device used to determine if the wearable master electronic device and the wearable node are worn by the same subject comprises a bioimpedance sensor.

A wearable master electronic device designated AG including the features of the wearable master electronic device designated AA-AF wherein the radio subsystem comprises a separate BAN radio and uplink radio.

A wearable master electronic device designated AH including the features of the wearable master electronic device designated AA-AF wherein the at least one processor is a plurality of processors, and wherein firmware for basic functions of the wearable master electronic device executes on a separate processor from the downloaded machine readable instructions.

A wearable master electronic device designated AJ including the features of the wearable master electronic device designated AE-AF wherein the memory further contains machine readable instructions for identifying a particular wearer wearing the wearable master electronic device from potential wearers recorded in a database.

A wearable master electronic device designated AK including the features of the wearable master electronic device designated AA-AJ wherein the memory further comprises specific machine-readable instructions capable of directing the processor to read data from a second sensor in the wearable node, the second sensor comprising a sensor selected from the group consisting of an electrocardiographic sensor, a glucose sensor, and an activity sensor.

A wearable master electronic device designated AL including the features of the wearable master electronic device designated AA-AK wherein the memory further comprises specific machine-readable instructions capable of directing the processor to configure the wearable node.

A wearable master electronic device designated AM including the features of the wearable master electronic device designated AL wherein the memory further comprises specific machine-readable instructions capable of directing the processor to configure an actuator of the wearable node.

A wearable master electronic device designated AN including the features of the wearable master electronic device designated AM wherein the actuator is selected from the group consisting of an electronic stimulator, an insulin pump, and a chemotherapy pump.

A wearable master electronic device designated AO including the features of the wearable master electronic device designated A and AA-AN wherein the memory further contains machine readable instructions for identifying a particular wearer wearing the wearable master electronic device from potential wearers recorded in a database.

A wearable master electronic device designated B including at least one processor with a memory, the at least one processor being coupled to a radio subsystem; at least one sensor configured for observing a biometric of a wearer, the biometric selected from the group consisting of vocal resonance, and bioimpedance; the memory further including machine-readable instructions capable of directing the processor to execute a classifier, the classifier configured to identify a wearer from wearer records in a database of potential wearers by using biometric sensor readings of a sensor selected from the group consisting of the at least one sensor and a sensor of a wearable node in communication with the wearable node over the radio subsystem.

A wearable master electronic device designated BA including features of the wearable master electronic device designated B wherein the radio subsystem is configured to communicate with a second node of a body area network (BAN), and the memory further comprises machine readable instructions for reading second sensor data from a sensor of the second node, and for processing the second sensor data to confirm that the second node and the wearable master electronic device are worn by the same wearer.

A wearable master electronic device designated BB including features of the wearable master electronic device designated B or BA wherein the memory further comprises machine-readable instructions capable of directing the processor to communicate through the radio subsystem to download specific machine-executable instructions associated with the wearable node from a server.

A wearable master electronic device designated BC including features of the wearable master electronic device designated B-BA or BD-BJ wherein the machine-readable instructions capable of directing the processor to communicate through the BAN radio comprise machine-readable instructions for encrypting communications.

A wearable master electronic device designated BD including features of the wearable master electronic device designated B, BA, or BB wherein the memory further comprises specific machine-readable instructions capable of directing the processor to read data from an additional sensor in at least one node of the BAN, the additional sensor comprising a sensor selected from the group consisting of an electrocardiographic sensor, a glucose sensor, and an activity sensor.

A wearable master electronic device designated BE including features of the wearable master electronic device designated B, BA, BB, or BD wherein the memory further comprises specific machine-readable instructions capable of directing the processor to configure the wearable node.

A wearable master electronic device designated BF including features of the wearable master electronic device designated BE wherein the memory further comprises specific machine-readable instructions capable of directing the processor to configure an actuator of the wearable node.

A wearable master electronic device designated BG including features of the wearable master electronic device designated BF wherein the actuator is selected from the group consisting of an electronic stimulator, an insulin pump, and a chemotherapy pump.

A wearable master electronic device designated BH including features of the wearable master electronic device designated B, BA, BB, or BD-BG where the sensor providing sensor readings to the classifier is a bioimpedance sensor.

A wearable master electronic device designated BJ including features of the wearable master electronic device designated B, BA, BB or BD-BH wherein the sensor providing sensor readings to the classifier is a microphone.

A wearable master electronic device designated ABA including features of any of the wearable master electronic device designated A, AA-AN, B, or BA-BJ, wherein the device is configured to determine when it is placed in contact with a wearer and operations selected from the group consisting of identifying a wearer and downloading machine readable instructions associated with a wearable node occur when the device is placed in contact with a wearer.

While the invention has been particularly shown and described with reference to specific embodiments thereof, it will be understood by those skilled in the art that various other changes in the form and details may be made without departing from the spirit and scope of the invention. It is to be understood that various changes may be made in adapting the invention to different embodiments without departing from the broader inventive concepts disclosed herein and comprehended by the claims that follow.

What is claimed is:

1. A wearable master electronic device comprising:
at least one processor with a memory, the processor being coupled to a radio subsystem, the radio subsystem comprising at least one radio, the radio subsystem configured to provide a body area network (BAN) radio function to communicate with nodes of a BAN and to provide an uplink radio function for communications with a server;
the memory comprising machine-readable instructions capable of directing the processor to identify a wearable node of the nodes of the BAN and to communicate through the BAN radio with at least one wearable node to receive data therefrom, and machine-readable instructions capable of directing the processor to communicate through the uplink radio to download an application comprising specific machine-executable instructions associated with the wearable node for processing data from that wearable node, to use the downloaded application to process data from that wearable node, and to upload data from the wearable node to a server;
at least one sensor;
wherein the memory further comprises machine-executable instructions capable of directing the processor to process readings from the at least one sensor and readings from at least a second sensor in the wearable node to determine if the wearable node and the wearable master electronic device are worn by a same subject; wherein the sensors read by the machine executable instructions and processed to determine if the wearable node and the wearable master electronic device comprise sensors selected from the group consisting of accelerometers, microphones, and bioimpedance sensors.

2. The wearable master electronic device of claim 1 wherein the sensor of the wearable master electronic device used to determine if the wearable master electronic device and the wearable node are worn by the same subject comprises an accelerometer.

3. The wearable master electronic device of claim 2 wherein the machine-readable instructions capable of directing the processor to process readings from the sensors to determine if the wearable node and wearable master electronic device are worn by the same subject comprise instructions for extracting features from data read from the sensors and deriving coherence of the features.

4. The wearable master electronic device of claim 3 wherein the radio subsystem comprises a separate BAN radio and uplink radio.

5. The wearable master electronic device of claim 1 wherein the sensor of the wearable master electronic device used to determine if the wearable master electronic device and the wearable node are worn by the same subject comprises a pulse sensor.

6. The wearable master electronic device of claim 1 wherein the sensor of the wearable master electronic device used to determine if the wearable master electronic device and the wearable node are worn by the same subject comprises a microphone.

7. The wearable master electronic device of claim 1 wherein the sensor of the wearable master electronic device used to determine if the wearable master electronic device and the wearable node are worn by the same subject comprises a bioimpedance sensor.

8. The wearable master electronic device of claim 7 wherein the radio subsystem comprises a separate BAN radio and uplink radio.

9. The wearable master electronic device of claim 1 wherein the at least one processor is a plurality of processors, and wherein firmware for basic functions of the wearable master electronic device executes on a separate processor from the downloaded machine readable instructions.

10. The wearable master electronic device of claim 7 wherein the memory further contains machine readable instructions for identifying a particular wearer wearing the wearable master electronic device from potential wearers recorded in a database.

11. The wearable master electronic device of claim 9 wherein the memory further comprises specific machine-readable instructions capable of directing the processor to read data from a second sensor in the wearable node, the second sensor comprising a sensor selected from the group consisting of an electrocardiographic sensor, a glucose sensor, and an activity sensor.

12. The wearable master electronic device of claim 11 wherein the memory further comprises specific machine-readable instructions capable of directing the processor to configure the wearable node.

13. The wearable master electronic device of claim 12 wherein the memory further comprises specific machine-readable instructions capable of directing the processor to configure an actuator of the wearable node.

14. The wearable master electronic device of claim 13 wherein the actuator is selected from the group consisting of an electronic stimulator, an insulin pump, and a chemotherapy pump.

15. The wearable master electronic device of claim 14 wherein the memory further contains machine readable instructions for identifying a particular wearer wearing the wearable master electronic device from potential wearers recorded in a database.

16. A wearable master electronic device comprising:
at least one processor with a memory, the at least one processor being coupled to a radio subsystem;
at least one sensor configured for observing a biometric of a wearer, the biometric comprising bioimpedance;
the memory further comprising machine-readable instructions capable of directing the processor to execute a classifier, the classifier configured to identify a wearer from wearer records in a database of potential wearers by using biometric sensor readings comprising readings of a sensor selected from the group consisting of bioimpedance observed by the at least one sensor and a sensor configured to observe bioimpedance of a wearable node in communication with the wearable master electronic device over the radio subsystem.

17. The wearable master electronic device of claim 16 wherein the radio subsystem is configured to communicate with a second node of a body area network (BAN), and the memory further comprises machine readable instructions for reading second sensor data from a sensor of the second node, and for processing the second sensor data to confirm that the second node and the wearable master electronic device are worn by the same wearer.

18. The wearable master electronic device of claim 17 wherein the memory further comprises machine-readable instructions capable of directing the processor to communicate through the radio subsystem to download specific machine-executable instructions associated with the wearable node from a server.

19. The wearable master electronic device of claim 18 wherein the machine-readable instructions capable of directing the processor to communicate through the BAN radio comprise machine-readable instructions for encrypting communications.

20. The wearable master electronic device of claim 18 wherein the memory further comprises specific machine-readable instructions capable of directing the processor to read data from an additional sensor in at least one node of the BAN, the additional sensor comprising a sensor selected from the group consisting of an electrocardiographic sensor, a glucose sensor, and an activity sensor.

21. The wearable master electronic device of claim 18 wherein the memory further comprises specific machine-readable instructions capable of directing the processor to configure the wearable node.

22. The wearable master electronic device of claim 21 wherein the memory further comprises specific machine-readable instructions capable of directing the processor to configure an actuator of the wearable node.

23. The wearable master electronic device of claim 22 wherein the actuator is selected from the group consisting of an electronic stimulator, an insulin pump, and a chemotherapy pump.

24. The wearable master electronic device of one of claims 15-22 wherein the sensor providing sensor readings to the classifier further comprises a microphone.

25. The wearable master electronic device of claim 2 wherein the sensor of the wearable master electronic device used to determine if the wearable master electronic device and the wearable node are worn by the same subject further comprises a gyro.

26. The wearable master electronic device of claim 2, wherein the sensors read by the machine executable instructions and processed to determine if the wearable node and the wearable master electronic device comprise accelerometers, and where the machine readable instructions are configured to identify and correlate sensor readings associated with walking to determine when the wearable node and wearable master electronic device are worn by a same patient.

* * * * *